United States Patent

Otagiri et al.

Patent Number: 5,302,399
Date of Patent: Apr. 12, 1994

[54] SLOW-RELEASING PHARMACEUTICALS PREPARED WITH ALGINIC ACID

[75] Inventors: Masaki Otagiri; Teruko Imai, both of Kumamoto, Japan

[73] Assignee: Snow Brand Milk Products Co., Ltd., Sapporo, Japan

[21] Appl. No.: 852,624

[22] Filed: Mar. 12, 1992

Related U.S. Application Data

[63] Continuation of Ser. No. 444,161, Nov. 9, 1989, abandoned.

[30] Foreign Application Priority Data

Mar. 9, 1988 [JP] Japan .................... 63-055784
Sep. 2, 1988 [JP] Japan .................... 63-219747

[51] Int. Cl.⁵ ............................. A61K 9/62
[52] U.S. Cl. ......................... 424/493; 424/489; 424/499
[58] Field of Search ............... 424/489, 491, 492, 493

[56] References Cited

U.S. PATENT DOCUMENTS 4,401,456  8/1983  Connick ................... 71/88
4,973,469  11/1990  Mulligan et al. ......... 424/461

FOREIGN PATENT DOCUMENTS 0232155  12/1987  European Pat. Off.

OTHER PUBLICATIONS

WPIL Accession No. 85-247023.
Chemical Abstracts, vol. 103: No. 8, Aug. 26, 1985, p. 343, Abstract No. 59240b.

Primary Examiner—Thurman K. Page
Assistant Examiner—Neil Levy
Attorney, Agent, or Firm—Millen, White, Zelano, & Branigan

[57] ABSTRACT

A slow-releasing pharmaceutical easily prepared with alginic acid gel beads as a slow releasing carrier, and a basic medicament such as a beta-blocking agent or a calcium antagonistic agent therein, whereby the basic medicament can be relesed at a desired rate by means of oral administration, etc.

12 Claims, 7 Drawing Sheets

● : PINDOLOL ADMINISTERED IN POWDER FORM
▽ : PINDOLOL ADMINISTERED IN ULA ALGINIC ACID GEL BEADS
○ : PINDOLOL ADMINISTERED IL₂ ALGINIC ACID GEL BEADS
◐ : PINDOLOL ADMINISTERED IN NA ALGINIC ACID GEL BEADS
■ : PINDOLOL ADMINISTERED IN DA-20 ALGINIC ACID GEL BEADS

● : PINDOLOL ADMINISTERED IN POWDER FORM
◐ : PINDOLOL ADMINISTERED IN CALVISKEN R
○ : PINDOLOL ADMINISTERED IN ALGINIC ACID GEL BEADS
a : $P < 0.05$ TO POWDERED PINDOLOL

● : NIFEDIPINE IN POWDER FORM
○ : NIFEDIPINE IN ALGINIC ACID GEL BEADS

SLOW-RELEASING PHARMACEUTICALS PREPARED WITH ALGINIC ACID

This is a continuation of application Ser. No. 07/444,161, filed Nov. 9, 1989, abandoned.

FIELD OF THE INVENTION

This invention relates to a slow-releasing pharmaceutical in which a basic medicament is contained in alginic acid gel beads and to a method for the production of the same.

DESCRIPTION OF THE PRIOR ART

Recently, the preparations of slow-releasing pharmaceuticals have been designed for the purpose of improving effectiveness and the safety of medicaments since slow-releasing pharmaceuticals reduce the number of doses, retain the expression of specified effects or reduce the incidence of side effects or toxicity as compared to ordinary fast-releasing pharmaceuticals.

Regarding these slow-releasing pharamaeuticals, in order to control the rate of release of medicaments in the body, various pharmaceuticals forms such as microcapsules, nano-capsules and matrices using various natural polymers, synthetic polymers, synthetic elastomers or the like have been suggested. For example, Shigeru Goto and Masakazu Kawada ("New Pharmaceutical Development System General Technology Design" R&D Planning Company, p.140, 1986) disclosed preparation of microcapsules or nano-capsules. Furthermore, matrix preparations have been disclosed by M. Bamba et al. (Int. J. Pharmaceut., 2307, 1979) and F. A. Kincl et al. (Archiv. Pharm., 317, 1984) and R. V. Sparer et al. (J. Contr. Release, 1, 23, 1984).

However, these preparations have problems such that the choice of combinations of medicaments and polymers and the processes employed for the preparation of slow-releasing pharmaceuticals thereby are complex.

The present inventors found that a pharmaceutical having a sufficiently slow-releasing property can be obtained by such simple means that a basic medicament is contained in alginic acid gel beads prepared with a polysaccharide, alginic acid which is a kind of natural polymer and a constituent of the cell membrane of brown algae.

Further, alginic acid is commercially available in forms of sodium salts having various molecular weight. Since alginic acid is slowly dissolved in water and highly viscous, it is used as a stabilizer or viscous agent in viscous foods such as ice cream, cheese, sherbet and syrup and also used in manufacturing films and fabrics.

SUMMARY OF THE INVENTION

Objects of the present invention are to provide a pharmaceutical form of a basic medicament having desirable slow-releasing properties using alginic acid gels, and to provide a method for the preparation of the same.

A slow-releasing pharmaceutical of the present invention is characterized by including a basic medicament in an acidic alginic acid gel beads so as to provide preferable binding features and to give preferable slow-releasing effects.

BRIEF DESCRIPTION OF THE DRAWINGS

Furthermore.

DETAILED DISCLOSURE

Figure 1:
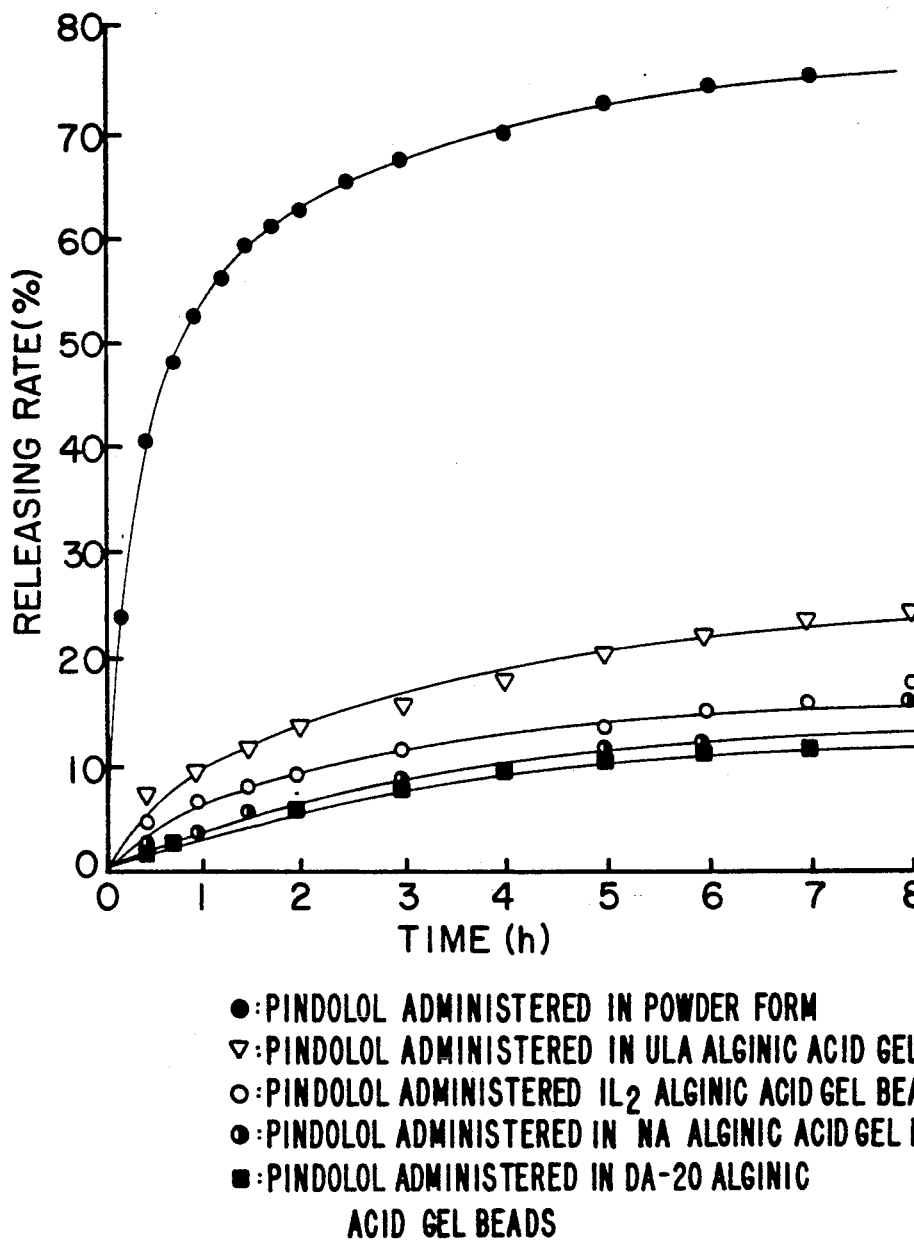
FIG. 1 shows the release of pindolol from the alginic acid gel beads in Example 1.

Examples of the basic medicaments used in the present invention include beta-blocking agents such as pindolol, procaterol, propranolol, pyltelol, and befunolol; calcium antagonists such as nifedipine, verapamil, diltiazem, and nicardipine; antihistamine agents such as difenhydramine, diphenylpyraline and chlorophenylamine; diuretics such as triamterene and penflutizide, vasodilative agents such as cinnarizine, ifenprodil, and pentoxifylline; and antitusives such as eprazinone, chloroprenaline, chloperastine, trimethoquinol, bromhexine, methoxyphenamine and sulbutanol.

In the present invention, alginic acid gel beads containing the above basic medicaments can be prepared using commercially available sodium alginates. However, in order to accomplish continuous and appropriate release of medicaments, particularly, sodium alginates having a molecular weight of about 10,000–100,000 are preferably used. 1% solutions of such sodium alginates have a viscosities of less than 100 cps and are useful in designing a preferable releasing system by selecting suitable sodium alginate depending on the kinds of medicament and releasing patterns.

In the present invention, alginates having the following features were used.

| Sodium alginate | MM/GG | Viscosity (cp) |
|---|---|---|
| No. 1 | 0.13 | 13.3 |
| No. 2 | 0.66 | 13.7 |
| No. 3 | 1.77 | 12.1 |

Consequently, as for the alginic acid gel, it has been determined that the release of the above-mentioned medicaments are affected by the difference in the ratio ( M/G ratio) of constituent sugars of the alginic acid, i.e., mannouronic acid (M) and guluronic acid (G). Further, it has also been revealed that the above-mentioned release is affected by the ratio of homo-block (MM) of mannuronic acid (M) and homo-block (GG) of guluronic acid (G) and furthermore the viscosity of alginic acid. Herein, the homo-block (MM, GG) means a block in which the same uranic acid (M or G), is sequenced.

In other words, when the amount of guluronic acid in the sugar composition increases, the matrix becomes so dense that the release of a medicament in the alginic acid gel beads becomes difficult. Also, when the MM/GG ratio is small, for example 0.13, the medicament can be released slowly.

According to the present invention, alginic acid gel beads which contain a basic medicament can be prepared as follows:

A basic medicament is suspended in a 4% sodium alginate solution and added drop by drop through a nozzle to a 0.1M $CaCl_2$ solution. The solution is allowed to stand for 72 hours and then alginic acid gel beads containing the basic medicament are collected by filtration. The alginic acid gel beads are dried in air for 24 hours and then dried in vacuo at room temperature for 24 hours.

In the above process, the molecular weight of the sodium alginate greatly affects both the yield of alginic acid gel beads formed and the content of the medicament contained in the alginic acid gel beads. With a view to controlling the release, alginic acid having a low viscosity, i.e. a low molecular weight, is preferably used.

Prior to preparation, the concentration of the basic medicament should be determined by considering the amount necessary to achieve the desired release.

According to the present invention, the alginic acid gel beads containing a basic medicament, thus obtained, can be formulated as necessary, for example, into enteric coated pills.

Further, a pharmaceutical according to the present invention can be expected to control the absorption of sodium in the body, since alginic acid forms gel structures by binding to calcium and thus calcium is replaced by sodium when the alginic acid is diffused to release the medicament therefrom in the intestine.

A process for the preparation of the slow-releasing pharmaceutical of the present invention and releasing effects of the same are explained more in detail by the following Examples.

EXAMPLE 1

Preparation of Alginic Acid Gel Beads

As a basic medicament, a beta-blocking agent, pindolol, was suspended in a 4% sodium alginate solution ( M/G ratio of alginic acid=0.6) to make a pindolol concentration to 4% and the resultant suspension was added drop by drop using a nozzle into a 0.1M $CaCl_2$ solution. The resultant mixture was allowed to stand for 72 hours so as to prepare alginic acid gel beads containing pindolol therein.

The gel beads thus obtained were collected by filtration, dried in air for 24 hours and then dried in vacuo for 24 hours at room temeprature. The resultant preparation was subjected to a medicament releasing test, oral administration tests in rabbits or beagle dogs and an absorption test of the medicament in humans.

The sodium alginates used were as follows:
(1) A product of Kimizu Chemicals, sodium alginate with low viscosity ($IL_2$), the viscosity of a 1% solution: 20–50 cps;
(2) A product of Kimizu Chemicals, sodium alginate of ultra low viscosity (ULA), the viscosity (10% solution): 500 cps;
(3) A product of Wako Pure Chemicals, reagent grade sodium alginate (NA), the viscosity (1%): 20 cps; and
(4) A product of Kibun Food Chemipha, Dack alginic acid (DA-20), the viscosity (1%): 20 cps.

Further, the pindolol content and yield in alginic acid gel beads are shown in Table 1.

TABLE 1

|  | Pindolol (%) | Recovery (%) |
|---|---|---|
| NA | 47.2 | 78.9 |
| $IL_2$ | 44.9 | 75.8 |
| ULA | 14.5 | 21.5 |
| DA-20 | 60.2 | 77.5 |

Medicament Releasing Test

Alginic acid gel beads containing 10 mg of pindolol as pindolol were suspended in 150 ml of water maintained at 37° C. The suspension was stirred at 150 rpm and the medicament released was measured at given intervals.

As shown in FIG. 1, the rate of the release of pindolol was much slower from the alginic acid gel beads than from pindolol by itself. Furthermore, the lower the viscosity of sodium alginate used (i.e., the smaller the degree of polymerization of alginic acid), the better was the release of pindolol.

Oral Administration Test in Rabbits

Male Japanese white rabbits (2.0–2.5 kg) were starved for 24 hours before the administration of medicaments.

alginic acid gel beads (30 mg/kg as pindolol) was administered with 100 ml of the alginic acid gel beads to the test animals and 3 ml of blood sample was taken from the auricular veins of each animals at given intervals. The samples were centrifuged and 1 ml each of serum was obtained. Pindolol was extracted from the serum and was quantatively measured by high performance liquid chromatography (HPLC).

Figure 2:
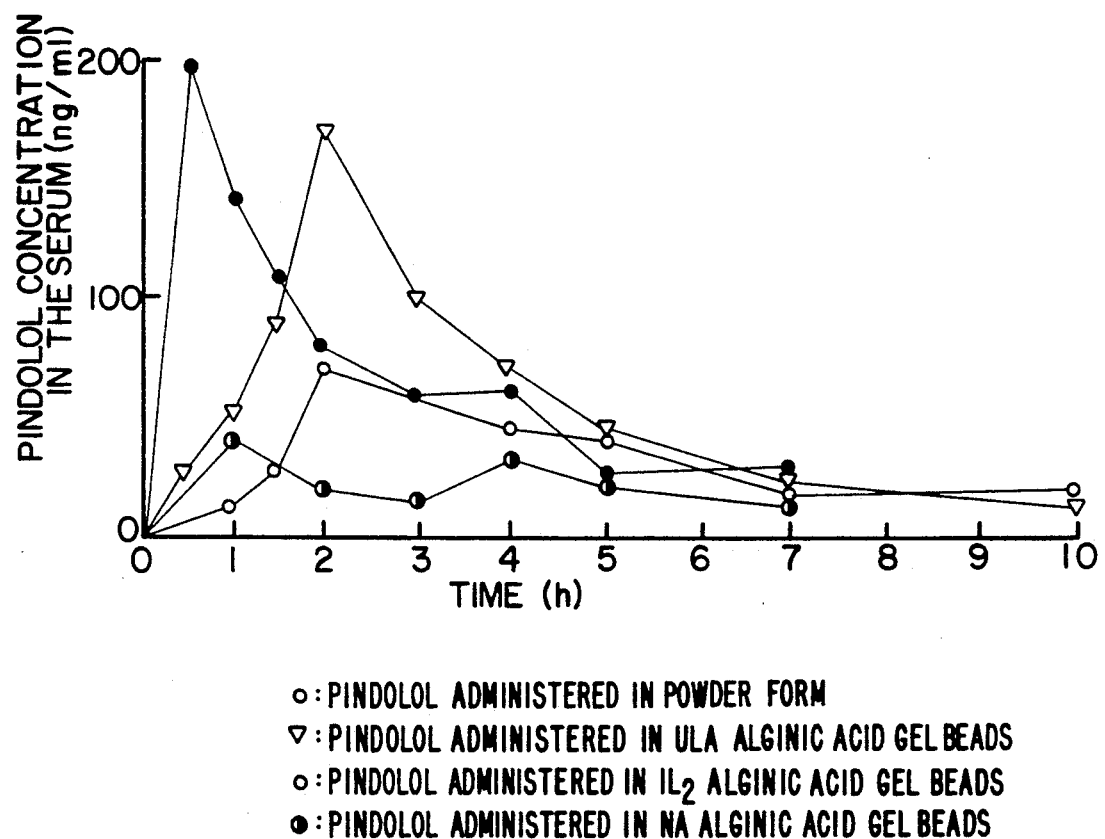
FIG. 2 shows the change in the serum pindolol concentration after oral administration of the alginic acid gel beads to rabbits.

As shown in FIG. 2, the pindolol concentration transferred to the serum after the oral administration to the rabbits was lower in the case of administration of pindolol as alginic acid gel beads than as pindolol by itself. As evident from the results, pindolol contained in the alginic acid gel beads was absorbed slowly, which showed slow-releasing effects. Moreover, the higher the viscosity of alginic acid, the smaller were the rate and amount of pindolol absorption. Consequently, it is considered that the pindolol concentration in the serum can be controlled by the combination of various kinds of alginic acid gel beads.

Oral Administration Test Using Beagle Dogs

Male beagle dogs (10 kg) were starved for 24 hours before the adminsitration of a test medicament. Water was given ad libitum.

In the case of the administration of pindolol by itself, a total amount 5 mg/kg of a powdered medicament was administered, i.e. 2.5 mg/kg with 20 ml of water at the start and 6 hours later. In the case of the administration of pindolol contained in alginic acid gel beads, 5 mg/kg was orally administered with 20 ml of water. Water was given ad libitum during the test period. At given intervals, 5 ml of blood was taken from the forefoot vein and centrifuged so as to obtain 2 ml each of the serum. The medicament was extracted from the serum and quantatively determined by high performance liquid chromatography (HPLC).

In this test, alginic acid gel beads prepared using the low viscosity alginic acid gel beads ($IL_2$, Kimizu Chemicals) were used.

Figure 3:
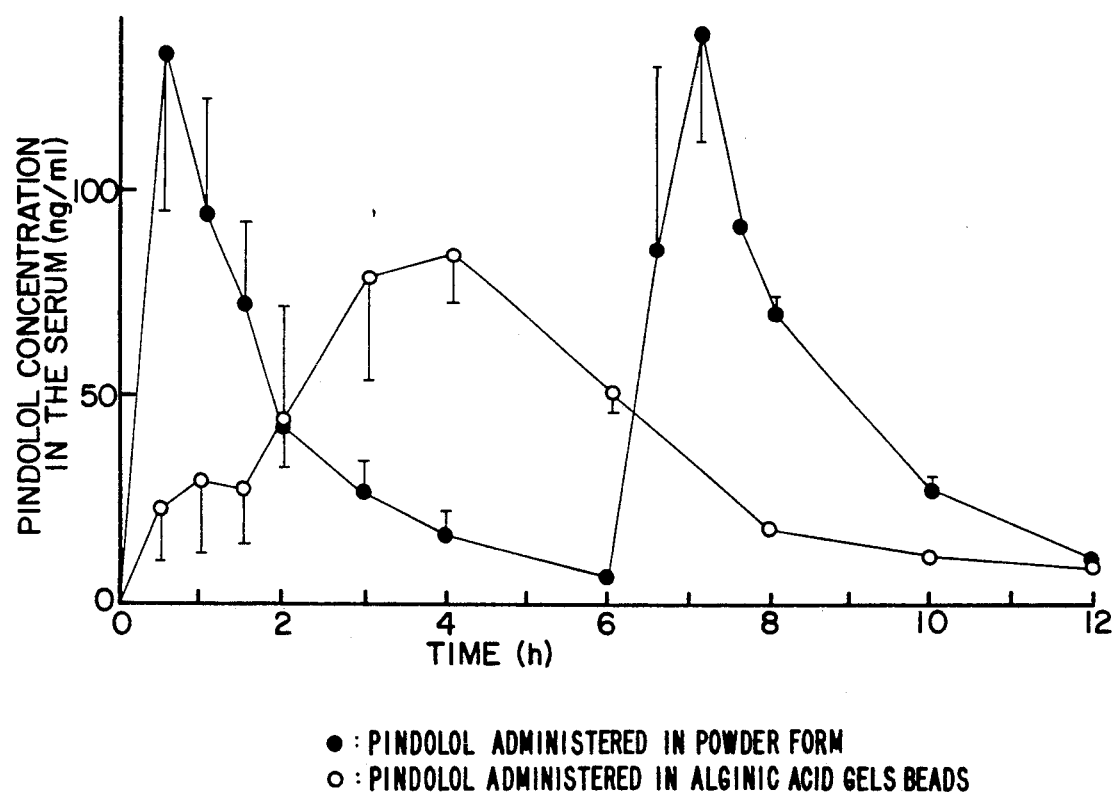
FIG. 3 shows the change in the serum pindolol concentration after oral administration of the alginic acid gel beads to beagle dogs.

Results are shown in FIG. 3.

Further, the results of the velocity analysis of the concentration of the medicament in the serum are shown in Table 2.

TABLE 2

| Form of preparation and time elaspsed | AUC (ngh/ml) | MRT (h) | VRT (h$^2$) |
|---|---|---|---|
| Pindolol powder | | | |
| 0 → 6 h | 238.0 | 1.74 | 1.74 |
| 0 → 12 h | 311.4 | 1.98 | 1.83 |
| Alginic acid gel beads | | | |
| 0 → 12 h | 445.7 | 4.62 | 5.93 |

AUC: Concentration in the serum - Area under the time curve
MRT: Mean retention time (average time in which the medicament retain in the body; the faster the absorption, the smaller the value of MRT.)
VRT: Variance of retention time (the longer the retention, the larger the value of VRT).

The results of this analysis revealed that pindolol contained in the alginic acid gel beads was absorbed more slowly and moreover retained activity longer than pindolol by itself. Namely, the slow-releasing effect by the use of alginic acid gel beads was observed.

Absorption Test in Humans

The alginic acid gel beads (alginic acid having MM/GG=0.66 was used) that was revealed to be the most advantageous slow-releasing pharmaceutical in the oral administration test mentioned above were orally administered to four healthy human adults and compared with a commercially available pindolol slow-releasing pharmaceutical, Calvisken (registered trademark, Sankyo Co., Ltd.). Calvisken is a release-retaining nucleated double-layered tablet in which 10 mg each of pindolol is contained in the core tablet and in the outer layer and the enteric coat is coated on the core tablet.

Figure 4:
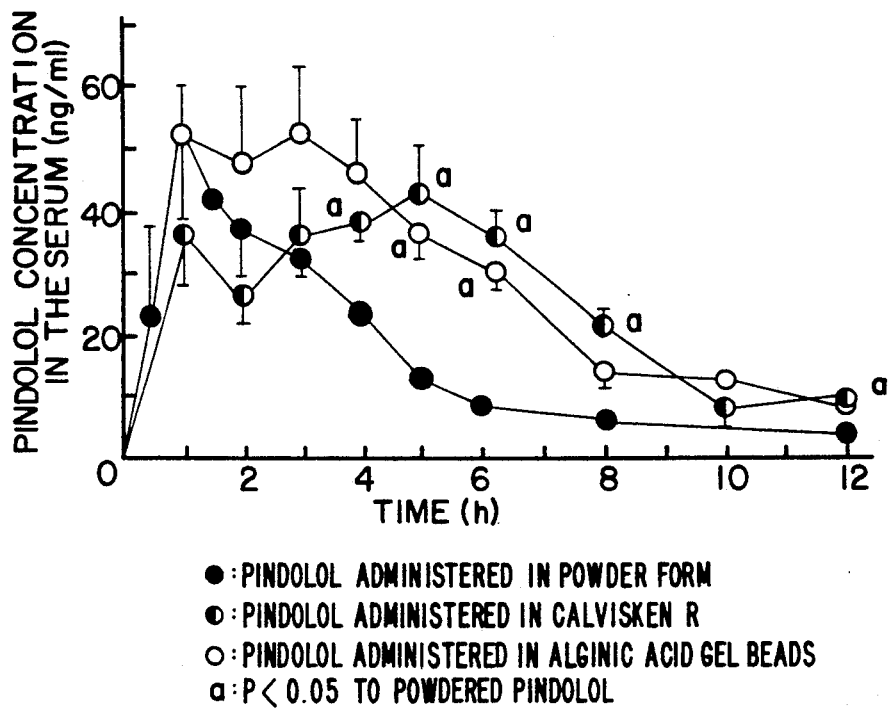
FIG. 4 shows the absorption of pindolol in the alginic acid gel beads in beagle dogs.

FIG. 4 shows the change of pindolol concentration in the serum (figures are the average±standard deviation for the 4 adults). In the case where powdery pindolol was orally administered in an amount of half (10 mg) of the slow-releasing pharmaceutical, $T_{max}$ (time to reach the maximum serum concentration) was about 1 hour and the medicament in the serum was thereafter gradually disappeared. On the other hand, in the case of the two kinds of the slow-releasing pharmaceuticals, for 1 to 6 hours after the administration, the pindolol concentration in the serum was maintained comparative to $C_{max}$ (maximum serum concentration) after the administration of powdery pindolol; thus it was confirmed that the alginic acid gel beads was biologically equivalent to calvisken R. Since the effective concentration of pindolol in the serum is 10–50 ng/ml, in the case of the alginic acid gel beads, the serum pindolol concentration is rather exceedingly high for 3 hours after the administration. However, the effective pindolol concentration in the serum was maintained for 10 hours after the administration. Velocity parameters obtained by the analysis of the change in the concentration in the serum are shown in Table 3.

TABLE 3

| Form of preparation | AUC (ng h/ml) | MRT (h) | VRT (h$^2$) |
|---|---|---|---|
| Pindolol powder | 377.5 ± 48.5* | 3.82 ± 0.32 | 7.44 ± 0.54 |
| Alginic acid gel beads | 336.3 ± 43.3** | 4.66 ± 0.42$^{a)}$ | 8.16 ± 0.47 |
| Calvisken R | 305.7 ± 25.7** | 5.07 ± 0.30$^{a)}$ | 7.49 ± 0.37 |

Note:
*AUC$_{0-6}$ × 2
**AUC$_{0-12}$
$^{a)}$p < 0.05 to the value for powdery pindolol (Significantly different from that for powdery pindolol at the significance level of 5%)

As shown in Table 3, the AUCs after the administration of the slow-releasing pharmaceuticals were slightly smaller than the 2-fold of the AUC after the administration of powdery pindolol; but significant difference was not observed. Furthermore, the MRT for the slow-releasing pharmaceuticals is longer than that for the powdery pindolol; thus, the slow releasing effect was confirmed.

Consequently, it was clear that the alignic acid gel beads prepared according to this example were as effective as the commercially available slow-releasing tablet, Calvisken R; thus the usefulness of the alginic acid as a slow-releasing carrier was confirmed.

EXAMPLE 2

Preparation of Alginic Acid Gel Beads

As a basic medicament, a calcium antagonist, nifedipine, was suspended in a 4% low viscosity sodium alginate solution (IL$_2$, Kimizu Chemicals) to make a pindolol concentration to 4% and then the suspension was added drop by drop using a nozzle into a 0.1M CaCl$_2$ solution. The resultant mixture was allowed to stand for 72 hours so as to prepare alginic acid gel beads containing nifedipine.

The content of nifedipine in the gel beads thus obtained was 45%.

The gel beads were collected by filtration, dried in air for 24 hours and then dried in vacuo for 24 hours at room temperature. The resultant preparation was subjected to the medicament releasing test.

Medicament Releasing Test

The alginic acid gel beads corresponding to 10 mg as nifedipine were suspended in 150 ml of water maintained at 37° C. The suspension was stirred at 150 rpm and the medicament released was measured at given intervals.

Figure 5:
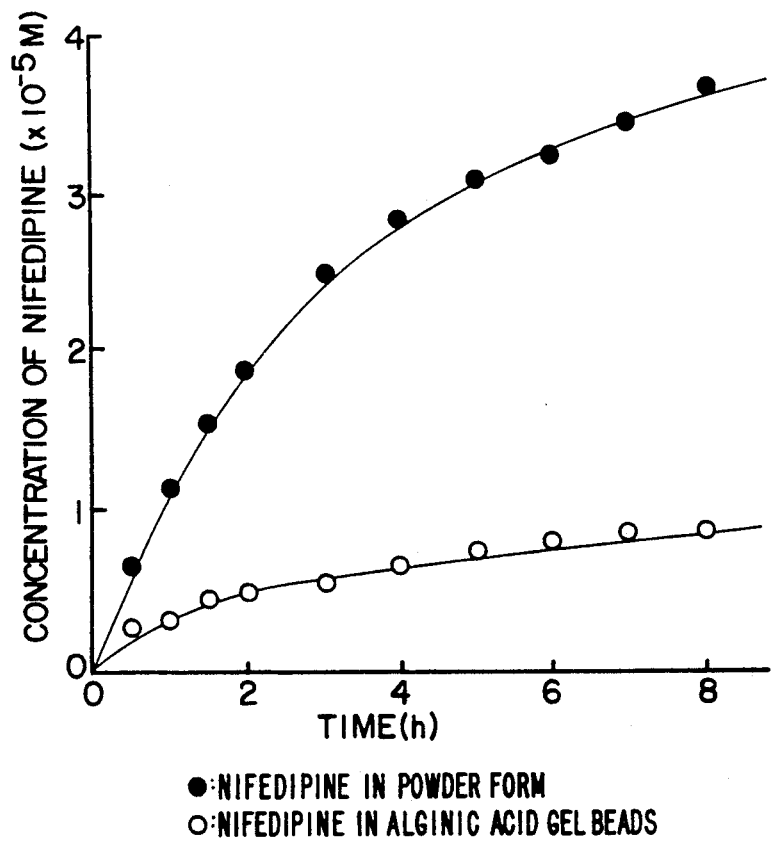
FIG. 5 shows release of nifedipine from the alginic acid gel beads in Example 2.

As shown in FIG. 5, the rate of the release of nifedipine was much slower from the alginic acid gel beads than from nifedipine by itself.

Absorption Test in Beagle Dogs

The oral administration to beagle dogs was carried out in the same manner as described in Example 1 using pindolol. The nifedipine concentration in the serum was determined in the same manner as described in Example 1.

Figure 6:
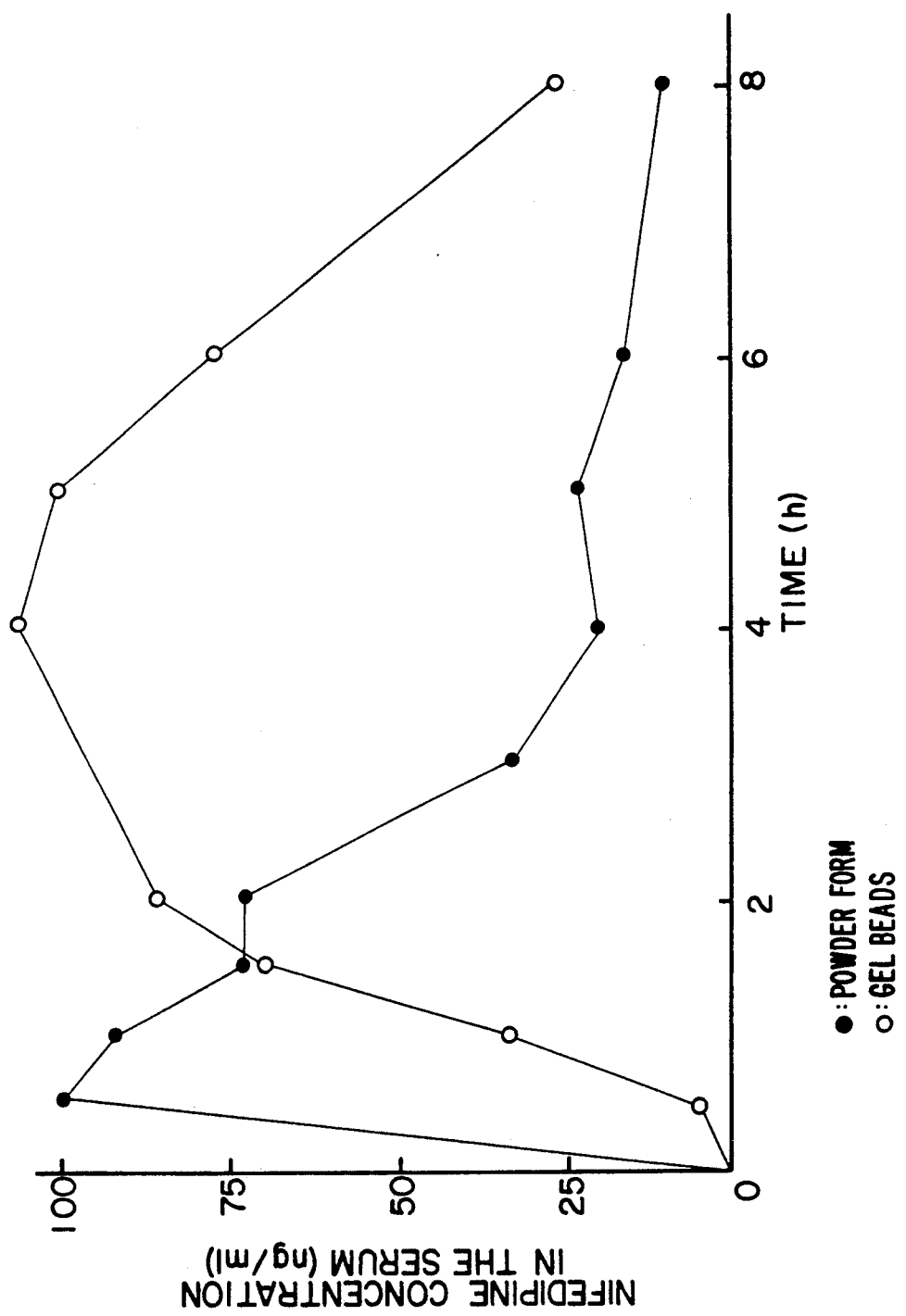
FIG. 6 shows the absorption of nifedipine contained in alginic acid gel beads.

As shown in FIG. 6, nifedipine contained in the alginic acid gel beads was absorbed more slowly and more extensively than pindolol in powder form.

EXAMPLE 3

This example is carried out to demonstrate the effect of the ratio of mannuronic acid and guluronic acid (M/G ratio) in the constituent sugar in alginic acid used for alginic acid gel beads on the slow releasing effect of a medicament.

Preparation of Alginic Acid Gel Beads

Sodium alginates having the M/G ratios of 0.5, 1.3 and 2.4 were used. Alginic acid gel beads were individually prepared in the same manner as described in Example 1.

Figure 7:
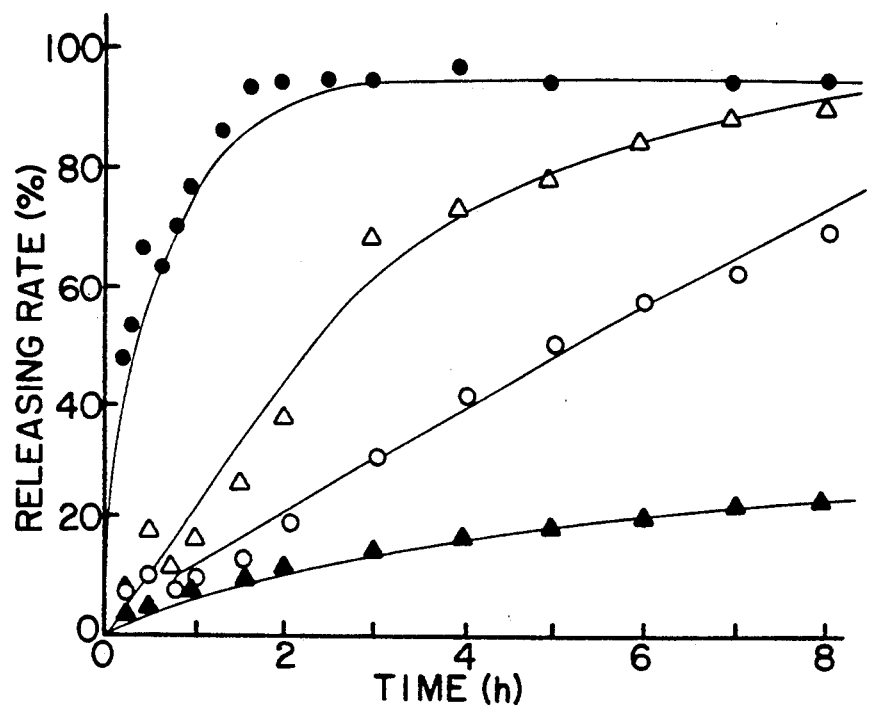
FIG. 7 shows the releasing effect of alginic acid gel beads with the M/G ratio of 1:3 as compared to alginic acid gel beads with other M/G ratios.
Figure 8:
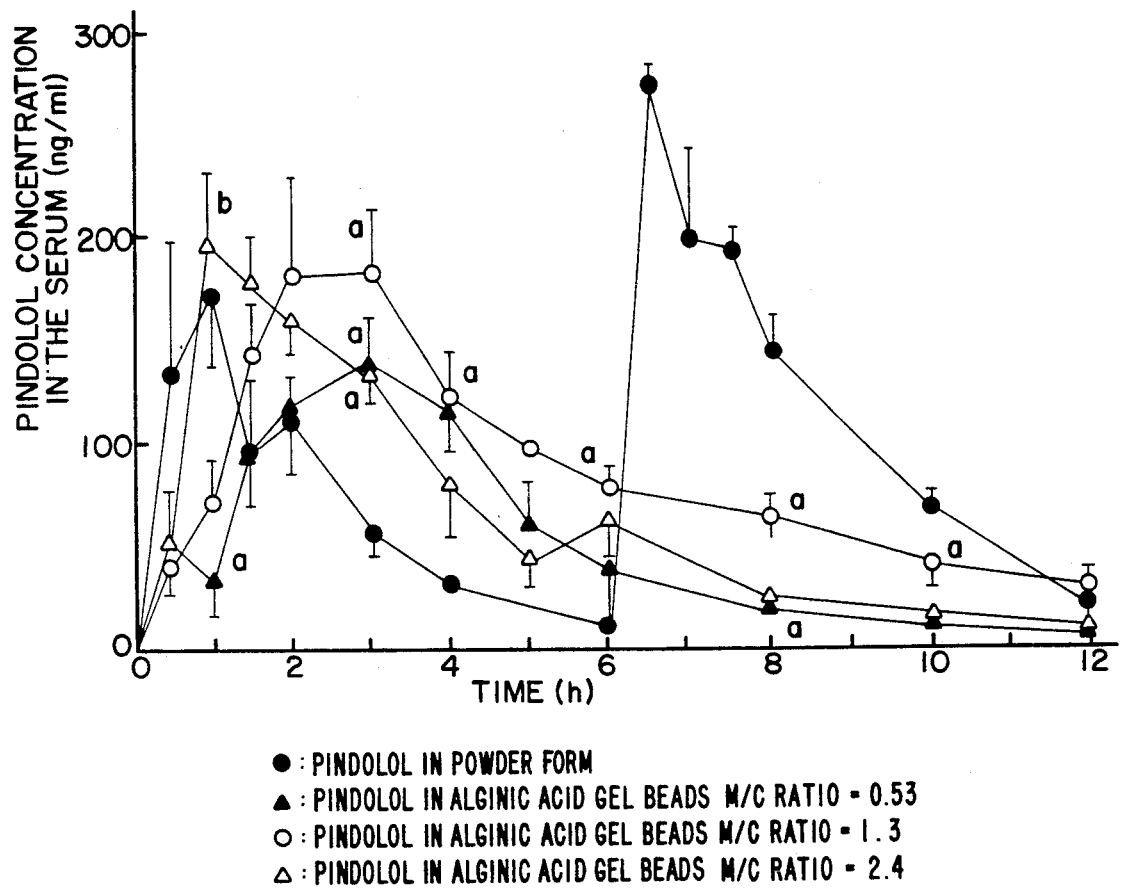
FIG. 8 shows the change of the scrum pindolol concentration in beagle dogs orally administered with pindolol powder and with alginic acid gel beads with the same M/G ratio as above.

Then, the alginic acid gel beads thus obtained were subjected to the medicament releasing test according to the procedure described in Example 1 to investigate the releasing pattern of pindolol. As shown in FIG. 7, it was revealed that at the M/G ratio=1.3, the rate of the release of pindolol was appropriately controlled. Moreover, the oral administration test using beagle dogs was carried out in the same manner as in Example 1 so as to investigate the change in the concentration of pindolol in the serum. Results are shown in FIG. 8. As shown in FIG. 8, the advantage of the use of the alginic acid gel beads prepared using alginic acid having the M/G ratio=1.3 was observed.

Possible Industrial Use

A slow-releasing pharmaceutical of the present invention can be prepared containing a basic medicament in alginic acid gel beads, in which the M/G ratio, MM/GG ratio and the molecular weight of the alginic acid to be used are selected depending on the desired releasing rates and, furthermore, alginic acid gel beads having an appropriate matrix structure are easily prepared using a metal ion such as Ca ion or the like for the alginic acid gel formation. As a result, a pharmaceutical which exerts the desirable effect of slow-releasing of effective ingredients can be prepared.

Furthermore, since the pharmaceutical of the present invention exerts the slow-releasing effect also by ordinary oral administration, it is extensively applicable in the field of medicine. In particular, it is extremely useful in the field where retention of the effect of efficacious ingredients and reduction in the number of dose are desirable or in the field where manifestation of side effects or toxicity due to prompt effectiveness is apprehended.

Furthermore, the slow releasing pharmaceutical prepared with the alginic acid gel beads according to the present invention is extensively applicable in various kinds of chemical reactions as a catalyst or additive. Furthermore, the alginic acid gel beads are widely applicable to a fertilizer, agricultural chemical, soil chemicals, food additive or the like because the gel beads can be easily formulated into various forms.

I claim:

1. In a process for the production of alginate gel beads containing a particulate bioactive material dispersed therein by the steps of adding a solution of a water soluble salt of alginic acid which contains the bioactive material dispersed therein dropwise into a solution of gellant for the alginic acid, thereby producing the beads and then separating and drying the thus-produced beads, the improvement which comprises the combination of employing as the bioactive material a suspension in the starting solution of particles of a basic medicament adapted for oral ingestion; employing $CaCl_2$ as the gellant; and employing as the starting solution of a water soluble salt of alginic acid, a 4% solution of the sodium salt of an alginic acid which has a molecular weight of about 10,000–100,000, a ratio of homo-block (MM) mannuronic acid to homo-block (GG) guluronic acid therein of from 0.13 to 1.77 and a viscosity, as a 1% solution of the sodium salt thereof, of less than 100 cps, thereby producing beads in which the rate of release of the basic medicament from the beads upon ingestion thereof is controlled.

2. Alginate gel beads produced according to the process of claim 1.

3. The alginate gel beads composition as set forth in claim 2, wherein the basic medicament is a beta-blocking agent.

4. The alginate gel beads composition as set forth in claim 3, wherein the beta-blocking agent is pindolol.

5. The alginate gel beads as set forth in claim 2, wherein the basic medicament is a calcium antagonistic agent.

6. The alginate gel beads composition as set forth in claim 5, wherein the calcium antagonistic agent is nifedipine.

7. The process as set forth in claim 1, wherein the solution contains 4% of the basic medicament suspended therein.

8. The process of claim 7, wherein the basic medicament is pindolol.

9. The process of claim 7, wherein the basic medicament is nifedipine.

10. The process as set forth in claim 1, wherein the suspension is added dropwise through a nozzle to the calcium chloride solution and then allowed to stand for about 72 hours.

11. The process as set forth in claim 1, wherein the viscosity (1% solution) is from 13.3 to 12.1.

12. The process of claim 1, wherein the basic medicament is pindolol or nifedipine and the solution contains 4% of sodium alginate, and wherein the suspension is added dropwise through a nozzle to the calcium chloride solution and then allowed to stand for about 72 hours.

* * * * *

UNITED STATES PATENT AND TRADEMARK OFFICE
CERTIFICATE OF CORRECTION

PATENT NO. : 5,302,399
DATED : April 12, 1994
INVENTOR(S) : Masaki OTAGIRI et al.

It is certified that error appears in the above-identified patent and that said Letters Patent is hereby corrected as shown below:

Title Page: Item (30) Foreign Application Priority Data:

Insert - - PCT/JP89/00255  March 09, 1989 - -

Signed and Sealed this

Ninth Day of August, 1994

Attest:

BRUCE LEHMAN

Attesting Officer

Commissioner of Patents and Trademarks